United States Patent [19]

Isono

[11] 4,376,051
[45] Mar. 8, 1983

[54] STERILIZATION OF AN ARTIFICIAL ORGAN

[75] Inventor: Keinosuke Isono, Kawaguchi, Japan

[73] Assignee: Terumo Corporation, Tokyo, Japan

[21] Appl. No.: 212,726

[22] PCT Filed: Mar. 5, 1980

[86] PCT No.: PCT/JP80/00039
§ 371 Date: Oct. 31, 1980
§ 102(e) Date: Oct. 31, 1980

[87] PCT Pub. No.: WO80/01876
PCT Pub. Date: Sep. 18, 1980

[30] Foreign Application Priority Data

Mar. 5, 1979 [JP] Japan .................. 54/25434

[51] Int. Cl.³ ............................. B01D 31/00
[52] U.S. Cl. .................. 210/321.3; 422/25; 422/38
[58] Field of Search ............ 210/232, 321, 433.2; 55/158, 159; 422/25, 48, 38; 128/DIG. 3; 261/DIG. 28

[56] References Cited

U.S. PATENT DOCUMENTS 3,880,759  4/1975  Van Assendelft .............. 210/194
4,176,156  11/1979  Asanuma et al. ........... 210/321.3 X

FOREIGN PATENT DOCUMENTS 53-48395   5/1978  Japan .
53-84394   7/1978  Japan .
53-84395   7/1978  Japan .
53-101890  9/1978  Japan .
54-103297  8/1979  Japan .

OTHER PUBLICATIONS

Technical Article Entitled, "Tests on the Influence of the γ-Irradiation and the Ethylene Oxide Sterilisation Over Cuprophan", Dr. Kr./Dr. Schl./Lu. Fr/w, Wuppertal, Aug. 30, 1976, pp. 2-9.

Primary Examiner—David R. Sadowski
Attorney, Agent, or Firm—Frishauf, Holtz, Goodman & Woodward

[57] ABSTRACT

An artificial organ embodying this invention is adapted for heat sterilization and allows for simple aftertreatment following said heat sterilization. The artificial organ is previously filled with a solution (8) harmless to the human body. A liquid pressure-buffering tube holding such an amount of gas as is capable of quantitatively absorbing the expansion of said solution (8) occurring during the heat sterilization of the artificial organ is connected to at least one of liquid ports (3), (4), (5), (6) communicating with the interior of the artificial organ. A process embodying the invention for heat sterilizing an artificial organ simplifies aftertreatment of said artificial organ following said heat sterilization, and comprises the steps of vacuum packaging the whole artificial organ device and heat sterilizing the artificial organ device while a gas held in the liquid pressure-buffering tube (2) is kept in the upper part of said artificial organ device.

7 Claims, 3 Drawing Figures

STERILIZATION OF AN ARTIFICIAL ORGAN

FIELD OF THE INVENTION

This invention relates to an artificial organ and a method of thermally sterilizing said artificial organ which is adapted to thermally sterilize said artificial organ, for example, in an autoclave and eliminates the necessity of carrying out an aftertreatment following said thermal sterilization.

BACKGROUND OF THE INVENTION

The known processes of sterilizing an artificial organ, for example an artificial kidney, includes the step of filling such artificial organ with an aqueous solution of a sterilizer, such as formalin, or the step of filling said artificial organ with a sterilizing gas of, for example, ethylene oxide. Since the sterilizer is harmful to the human body, the prior art process of sterilizing an artificial organ makes it necessary to wash the interior of an artificial organ before it is applied to the human body. In this case, various difficulties arise that where a solution of a sterilizer, for example, formalin filled in an artificial organ is replaced by a physiological sodium chloride solution, then formaldehyde is left, and moreover harmful substances such as chlorohydrin are produced, and complete elimination of a sterilizer, for example, involves a great deal of time and work. Consequently, the conventional process of sterilizing an artificial organ has not been regarded as satisfactory.

To avoid the above-mentioned problems, a process has been proposed which comprises fully filling the interior of an artificial organ with a physiological sodium chloride solution, instead of applying any of the abovementioned chemical sterilizers and sterilizing the artificial organ with pressure and heat in an autoclave. However, this proposed sterilizing process still has the drawbacks that the artificial organ tends to be cracked or broken due to the thermal expansion of the physiological sodium chloride solution filled in the artificial organ; and these difficulties have to be resolved, before said proposed sterilizing process can be satisfactorily put to practical use.

Processes proposed to date for resolution of the aforementioned problems include, for example, the step of conducting a cannula-bearing buffer bag through the blood port or dialyzate port of an artificial organ, sterilizing the artificial organ under such condition in an autoclave, removing the buffer bag after sterilization, packing the sterilized artificial organ in a wrapper, and again sterilizing the wrapped artificial organ with an ethylene oxide gas. Another proposed process comprises fitting a deformable bag-shaped cap to the blood port or dialyzate port of an artificial organ, sterilizing the artificial organ under such condition in an autoclave, removing the bag-shaped cap, fitting the ordinary rubber cap instead, and packing the assembly in an aseptic atmosphere. However, the above-mentioned proposed processes have the drawbacks that steps extending from the sterilization of an artificial organ in an autoclave to the production of a sterilized packed artificial organ are complicated and consume a great deal of time and work, and further during the aftertreatment following sterilization, the artificial organ is likely to be again contaminated by septic or other harmful microbes. With the former proposed artificial organ-sterilizing process based on the application of a cannula-bearing buffer bag, that portion of an artificial organ which is pierced by a cannula tends to be contaminated, for example, by molds, or bacteria. With the latter proposed artificial organ-sterilizing process based on the application of a bag-shaped cap, tremendous difficulties are encountered in replacing the bag-shaped cap with the ordinary cap and packing a sterilized artificial organ in an aseptic condition. With the above-mentioned proposed artificial organ-sterilizing processes, an artificial organ sterilizer in an autoclave is cooled by water before said organ is packed in the succeeding step. Therefore, care should be taken against the possible contamination of the artificial organ during the water-cooling step.

This invention has been accomplished in view of the above-mentioned circumstances, and is intended to provide an artificial organ and a method of sterilizing the same which is adapted for sterilization with heat and pressure, for example, in an autoclave. Thus, it eliminates the necessity of an aftertreatment of the sterilized artificial organ, and prominently facilitates the connection of the artificial organ, for example, to a blood circuit.

SUMMARY OF INVENTION

This invention provides an artificial organ characterized by:
a device body which contains a blood-treating mechanism and is fitted with a solution harmless to the human body;
blood ports or dialyzate ports communicating with the device body; and
a liquid pressure-buffering tube which communicates with at least one of the blood port and dialyzate port, and holds a sufficient amount of gas to quantitatively absorb the expansion of the solution which arises during the thermal sterilization of the artificial organ. With the artificial organ embodying this invention which is constructed as described above, the liquid pressure-buffering tube is made to communicate with the at least one of the blood port and dialyzate port of the artificial organ to absorb the expansion of the solution which occurs during the thermal sterilization of the artificial organ. Therefore, the whole of the artificial organ can be thermally sterilized effectively, while being sealed in a bag impermeable to bacteria or preferably vacuum-packed. Therefore, it is unnecessary to carry out sterilization again when the artificial organ is packed as is the case with the conventional artificial organ-sterilizing process, and also to take off a buffer bag after the thermal sterilization of the artificial bag, offering prominent advantages from the standpoint of sanitary precaution and also the steps of manufacturing an artificial organ.

With the above-mentioned artificial organ embodying this invention, the liquid pressure-buffering tube is preferred to be the type which does not substantially swell during the thermal sterilization step, because such unexpandable liquid pressure-buffering tube enables the whole artificial organ device to be easily sterilized in a packed state. As used herein, the term "does not substantially swell during the thermal sterilization" is defined to mean that the extent to which the liquid pressure-buffering tube is expanded by the heat applied in the thermal sterilization falls within the range in which the effect of packing the artificial organ is not substantially lost.

A method embodying this invention for thermally sterilizing an artificial organ which comprises a device body containing a blood-treating mechanism and at least one pair of liquid ports communicating with said device body is characterized in that a sufficient amount of a solution harmless to the human body is filled to substantially prevent any gas from being left in the device body; a liquid pressure-buffering tube holding such an amount of gas as is capable of quantitatively absorbing the expansion of the solution which takes place during the thermal sterilization of the artificial organ communicated with at least one of the aforementioned liquid ports; the assembly of the artificial organ is hermetically sealed in a bag impermeable to bacteria; and thermal sterilization is carried out while a gas phase held in the liquid pressure-buffering tube is positioned in the upper part of the device body.

An artificial organ-sterilizing process embodying this invention enables an artificial organ packed in a vacuum to be thermally sterilized effectively, eliminating the necessity of undertaking thermal sterilization again when the artificial organ is packed, and taking off a buffer bag after thermal sterilization, as is the case with the convention artificial organ-sterilizing process, thus offering prominent advantages from the standpoint of sanitary precaution and the steps of manufacturing an artificial organ.

As used herein, the form "artificial organ" is defined to include not only an artificial kidney or artificial liver but also any other medical treating instrument for treating blood or any other body fluid by conducting it therethrough.

The liquid pressure-buffering tube used in the method of this invention is prepared from, for example, polyolefins such as polycarbonate, and polypropylene, synthetic resins such as polyvinyl chloride, polyamide, polyesters and 2-methylpentene, metals or rubbers. It is practically preferred that the liquid pressure-buffering tube be constructed in a substantially unexpandable form. No particular limitation is imposed on the dimensions of the liquid pressure-buffering tube. However, this liquid pressure-buffering tube should preferably have that size, which, when an artificial organ is filled with a solution, causes a sufficiently large space to be left in said liquid pressure-buffering tube to quantitatively absorb the expansion of said solution when the artificial organ is thermally sterilized.

A solution previously filled in the device body may be formed of not only a physiological sodium chloride solution, but also an aqueous solution of heparin, an aqueous solution of glycerine, or a liquid harmless to the human body such as distilled water.

DETAILED DESCRIPTION OF THE INVENTION

Figure 1:
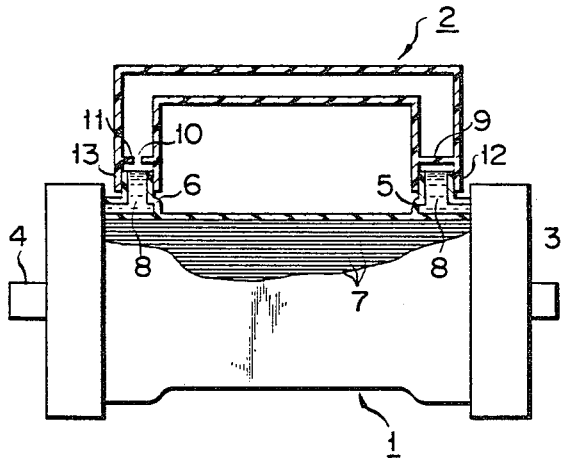
FIG. 1 is a lateral view partly in section of an artificial kidney device according to one embodiment of this invention.

FIG. 1 shows the arrangement of the known hollow fiber type artificial kidney to which this invention is applied. This artificial kidney device comprises a device body 1 and liquid pressure-buffering tube 2. The device body 1 is made into a substantially cylindrical form. Blood ports 3, 4 are projectively provided on both right and left sides of the device body 1. Dialyzate ports 5, 6 are provided in a state projecting in the same direction on those portions of the peripheral wall of the device body 1 which lie near to both right and left sides of the device body 1. The device body 1 contains a large number of hollow fibers 7 extending substantially in parallel lengthwise of the device body 1. The internal passages of the hollow fibers 7 communicate with the blood ports 3, 4. A space provided on the outer side of the hollow fibers 7 communicates with the dialyzate ports 5, 6. The interior of the device body 1, and the internal passages of the hollow fibers 7 are filled with a physiological sodium chloride solution 8 previously defoamed in a decompressed condition. Where the dialyzate ports 5, 6 are set in the upper port of the device body 1 before the artificial kidney is thermally sterilized, for example, in an autoclave, the physiological sodium chloride solution 8 is filled in such an amount as causes no space to be left in the cylindrical device body 1, or more preferably causes the dialyzate ports 5, 6 to be filled with said physiological sodium chloride solution 8.

The liquid pressure-buffering tube 2 is formed of a pipe prepared from an unexpandable material such as polypropylene or polycarbonate with a thickness of, for example 2 mm. Both ends 12, 13 of the liquid pressure-buffering tube 2 are engaged in airtightness with the openings of the dialyzate ports 5, 6 by means of a silicon rubber member. One end 12 of the liquid pressure-buffering tube 2 is fitted with a membrane 9 which completely closes the internal passage of the pressure-buffering tube 2. The other end 13 is provided with a membrane 11 having a fine orifice 10 allowing for the passage of a liquid. The space of that portion of the interior of the liquid pressure-buffering tube 2 which is defined between both membranes 9, 11 (a space for holding a gas) should be designed to have that volume which enables the volumetric expansion of the physiological sodium chloride solution 8 resulting from heating in an autoclave in which the artificial kidney is thermally sterilized to be fully absorbed by the contraction of a gas held in the liquid pressure-buffering tube 2, and further prevents a pressure prevailing in the whole interior of the device body 1 from rising beyond the limit pressure which the device body 1 can withstand. Now let it be assumed that where thermal sterilization is carried out while temperatures before and during said thermal sterilization are differentiated by about 100° C. and pressure during the thermal sterilization is rendered twice higher than that which prevails before said thermal sterilization, and pressures prevailing inside and outside of the liquid pressure-buffering tube 2 are kept in balance. In such case, the volume of a gas held in the liquid pressure-buffering tube 2 is compressed to substantially 66% of the original. This means that a liquid (for example, physiological sodium chloride solution) filled in the artificial kidney can be sucked into the liquid pressure-buffering tube 2 up to the remaining 34% of the total volume of said tube 2. If adhesion between the liquid pressure-buffering tube 2 and the dialyzate solution port 6 is effected with a sufficiently great force, then it will be possible to suck the liquid held in the artificial organ into the space of the liquid pressure-buffering tube 2 to a larger extent than 34% of the volume of said tube 2. Now let it be assumed that the device body has a total internal volume of 500 cm$^3$, and the liquid pressure-buffering tube 2 has an internal volume of 50 to 60 cm$^3$. Then an artificial organ can be thermally sterilized in an autoclave under the ordinary conditions, that is, at a temperature of 100° to 130° C., and pressure (gauge pressure) of 1 to 3 kg/cm$^2$ without causing a solution to leak from the sealed portion of the device body. No particular limitation is imposed on the size of a fine orifice 10 drilled in the membrane 11 provided at one end of the liquid pressure-buffering tube 2. However, said orifice 10 is preferred to be as small as possible in order to prevent air held in the liquid pressure-buffering tube 2 from being replaced by a physiological salt solution filled in the artificial organ. The membrane 11 may be directly fitted to the liquid pressure-buffering tube 2 or replaced by a different member. Namely, it is possible to cover, for example, the liquid port 6 with a silicone rubber tube having a fine orifice formed at one end and mount the liquid pressure-buffering tube 2 lacking the membrane 11 on said silicone rubber tube.

The above-described artificial kidney device is thermally sterilized through the steps of packing the main or whole part of said artificial kidney device in an airtight condition by vacuum packaging or any other means, holding said artificial kidney device in an autoclave with the liquid pressure-buffering tube 2 kept in the upper part of said artificial kidney device and applying pressure and heat at a prescribed level by the ordinary process. In this case, a physiological sodium chloride solution filled in the artificial kidney device flows into the liquid pressure-buffering tube 2 through the fine orifice 10 and is carried to the intermediate point of said tube 2. However, after the thermal sterilization, or preferably during cooling under pressure, the physiological sodium chloride solution regains the original position before the thermal sterilization. A thermally sterilized artificial kidney device is marketed or offered for practical application in a packed state, completely eliminating the necessity of carrying out aftertreatment following sterilization as is the case with the conventional artificial organ-sterilizing process.

Figure 2:
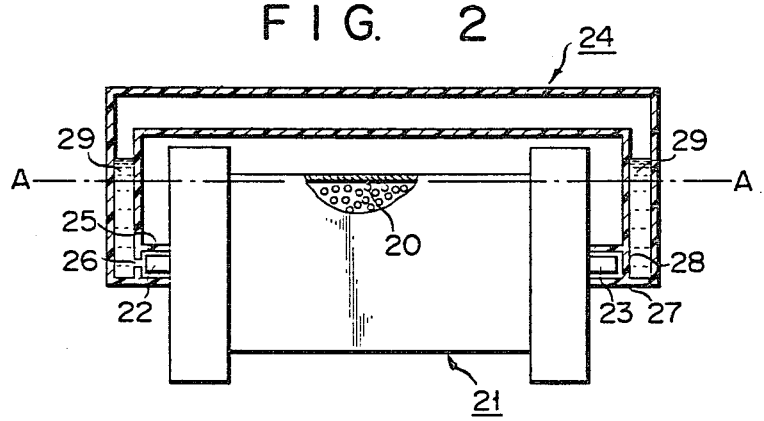
FIG. 2 is a lateral view partly in section of an artificial liver device according to another embodiment of the invention.

FIG. 2 schematically shows the arrangement of the known artificial liver device to which this invention is applied. This artificial liver device comprises a device body 21 filled with particles 20 of activated carbon, blood ports 22, 23 projectively provided at both ends of the device body 21 and a liquid pressure-buffering tube 24, both ends of which communicate with said blood ports 22, 23. The liquid pressure-buffering tube 24 is formed of an unexpandable material such as plastics or metal as in the embodiment of FIG. 1. One end 25 of the liquid pressure-buffering tube 24 communicates with the blood port 22 through a fine orifice 22. The other end 27 of said tube 24 is prevented from communicating with the blood port 23 by a membrane 28. The device body 21 is filled with a physiological sodium chloride solution 29 previously defoamed under a decompressed condition. In this case, care should be taken to cause the device body 1 to be filled with an amount of a physiological sodium chloride solution 29 as to leave no free space in the device body 1 before the thermal sterilization of the artificial liver, namely, causing the level of said physiological sodium chloride solution 29 to rise at least above line A of FIG. 2 when the liquid pressure-buffering tube 24 is positioned in the upper part of the device body 21. Further, it is necessary to allow a sufficient amount of gas to remain in the liquid pressure-buffering tube 24 to fully absorb the volumetric expansion of physiological sodium chloride solution 29 during the thermal sterilization of the artificial liver. Therefore, as in the case of the embodiment of FIG. 1, the internal volume of the pressure-buffering tube 24 should be rendered large enough to cause the volumetric expansion at the operating temperature of an autoclave of the physiological sodium chloride solution filled in the artificial liver to be fully absorbed by the compression of a gas held in said liquid pressure-buffering tube 24. Moreover, said internal volume should be determined with care taken to prevent the total internal pressure of the device body 21 from rising beyond the limit pressure which said device body 21 can withstand due to the volumetric expansion of the filled physiological sodium chloride solution during the thermal sterilization of the artificial organ.

As in the embodiment of FIG. 1, no particular limitation is imposed on the size and number of the fine orifice 26 drilled at one end of the liquid pressure-buffering tube 24. However, said orifice 26 is preferred to be as small as possible.

The artificial liver device according to the embodiment of FIG. 2 is thermally sterilized and operated in the same manner as the artificial kidney according to the embodiment of FIG. 1, and ensures the same effect. Before an artificial liver device is put to practical application, it is necessary to prevent a gas from being carried into said artificial liver device as rigidly as possible. Therefore, both ends 25, 27 should preferably be tightly closed by clamping means such as a clamp. It is possible to previously fit the clamp to the liquid pressure-buffering tube 24 before the artificial liver is packed and, later after the thermal sterilization of the artificial liver, manually control the operation of said clamp from above the packed assembly.

With respect to the embodiments of FIGS. 1 and 2, reference was made to the case where both ends of the liquid pressure-buffering tube were fixed to the blood ports. However, this invention is not limited to this arrangement. The closed end of the liquid pressure-buffering tube, namely, that end thereof which is not provided with fine orifices 10, 26 need not be fixed to a blood port or dialyzate port. Instead, said closed end may be connected to any other suitable part of the device body. Further, as shown in FIG. 3, said closed end may be used as a free end instead of being fixed in place.

Figure 3:
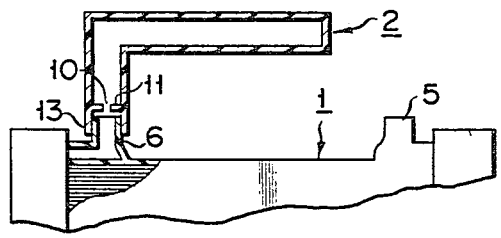
FIG. 3 is a lateral view of the main part of an artificial kidney device according to still another embodiment of the invention.

The reference numerals of FIG. 3 correspond to those of FIG. 1. The embodiment of FIG. 3 has substantially the same arrangement as that of FIG. 1, except that the closed end of the liquid pressure-buffering tube is used as a free end.

The foregoing description refers to the case where this invention was applied to an artificial kidney or artificial liver. Obviously, the invention is applicable to an artificial lung or a medical treating instrument for treating blood or any other body fluid. Further, reference was made to the case where one end of the liquid pressure-buffering tube communicated with the device body through a fine orifice and the other end thereof was closed. However, this invention is not limited to such an arrangement. Both ends of the liquid pressure-buffering tube may communicate with the device body. In the last mentioned case, however, it is advised to close at least one of both ends of the liquid pressure-buffering tube by clamping means after completion of the thermal sterilization of an artificial organ, for example, in an autoclave.

INDUSTRIAL APPLICABILITY

With an artificial organ and the process of sterilizing the same according to this invention, no harmful sterilizer is applied in sterilizing said artificial organ. Therefore, the present invention has the advantages that it is unnecessary to carry out aftertreatment following sterilization; that an artificial organ embodying the invention can be connected to a blood circuit in the form just as produced, offering considerable convenience in manufacturing, handling and energy saving; and that the invention is applicable to an artificial kidney, artificial liver, artificial lung and any other medical treating apparatus for treating blood or any other body fluid while it is flowing.

I claim:

1. In a heat sterilized artificial organ comprising:

a device body filled with an aqueous solution harmless to the human body;

at least one of blood ports and dialyzate ports in liquid communication with the device body; and a liquid pressure-buffering tube in liquid communication with at least one of said blood ports and dialyzate ports, and containing such an amount of gas as is capable of quantitatively absorbing the expansion of said aqueous solution during thermal sterilization of the artificial organ, said liquid pressure-buffering tube having two end portions;

the improvement wherein:

said liquid pressure-buffering tube being substantially unexpandable during thermal sterilization of the artificial organ, and comprising one end portion near said at least one of said blood and dialyzate ports with which said liquid pressure-buffering tube is in liquid communication, means defining a small orifice in said one end portion of said tube, said small orifice being dimensioned sufficiently small for preventing said gas within said liquid pressure-buffering tube from being replaced by said aqueous solution filled in said device body at normal ambient temperatures and for allowing the passage of said aqueous solution through said small orifice during heating of said artificial organ during sterilization thereof, said small orifice being smaller than the cross-sectional area of said port with which it communicates and smaller than the cross-sectional area of said liquid pressure-buffering tube at least in the vicinity of said port with which it communicates.

2. The artificial organ of claim 1, wherein at least one dialyzate port is provided in liquid communication with said device body; and said one end portion of said liquid pressure-buffering tube is coupled to and in liquid communication with said at least one dialyzate port, and the other end portion of said liquid pressure-buffering tube being closed.

3. The artificial organ of claim 2, wherein at least two dialyzate ports are provided liquid in communication with said device body; and said other end portion of said liquid pressure-buffering tube is coupled to a second of said at least two dialyzate ports.

4. The artificial organ of claim 1, wherein at least one blood port is provided in liquid communication with said device body; and said one end portion of said liquid pressure-buffering tube is coupled to and in liquid communication with said at least one blood port, and the other end portion of said liquid pressure-buffering tube being closed.

5. The artificial organ of claim 4, wherein at least two blood ports are provided liquid in communication with said device body; and said other end portion of said liquid pressure-buffering tube is coupled to a second of said at least two blood ports.

6. The artificial organ of claim 1, wherein each end portion of said liquid pressure-buffering tube is in liquid communication with a respective one of a pair of dialyzate ports.

7. The artificial organ of claim 1, wherein each end of said liquid pressure-buffering tube communicates with a respective one of a pair of blood ports.

* * * * *

UNITED STATES PATENT AND TRADEMARK OFFICE
CERTIFICATE OF CORRECTION

PATENT NO. : 4,376,051
DATED : March 8, 1983
INVENTOR(S) : Keinosuke ISONO

It is certified that error appears in the above-identified patent and that said Letters Patent is hereby corrected as shown below:

COLUMN 8 (claim 3), line 18, change "provided liquid in" to

--provided in liquid--;

COLUMN 8 (claim 5), line 30, change "provided liquid in" to

--provided in liquid--.

Signed and Sealed this

Twenty-fifth Day of October 1983

[SEAL]

Attest:

GERALD J. MOSSINGHOFF

Attesting Officer      Commissioner of Patents and Trademarks